(12) United States Patent
Doerr

(10) Patent No.: US 8,965,502 B2
(45) Date of Patent: Feb. 24, 2015

(54) CARDIAC STIMULATOR FOR CARDIAC CONTRACTILITY MODULATION

(71) Applicant: Biotronik SE & Co. KG, Berlin (DE)

(72) Inventor: Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 107 days.

(21) Appl. No.: 13/739,000

(22) Filed: Jan. 11, 2013

(65) Prior Publication Data

US 2013/0218222 A1    Aug. 22, 2013

Related U.S. Application Data

(60) Provisional application No. 61/599,432, filed on Feb. 16, 2012.

(51) Int. Cl.
*A61N 1/00* (2006.01)
*A61N 1/365* (2006.01)
*A61N 1/368* (2006.01)

(52) U.S. Cl.
CPC ............... *A61N 1/365* (2013.01); *A61N 1/368* (2013.01)
USPC .................................................. 607/9

(58) Field of Classification Search
CPC ............... A61N 1/3627; A61N 1/3628–1/3688
USPC ...................................................... 607/4–28
See application file for complete search history.

(56) References Cited

U.S. PATENT DOCUMENTS

| | | |
|---|---|---|
| 6,317,631 B1 | 11/2001 | Ben-Haim et al. |
| 6,360,126 B1 | 3/2002 | Mika et al. |
| 6,370,430 B1 | 4/2002 | Mika et al. |
| 2003/0120318 A1 | 6/2003 | Hauck |
| 2006/0247699 A1 | 11/2006 | Burnes et al. |
| 2009/0082825 A1 | 3/2009 | Arcot-Krishnamurthy et al. |
| 2010/0069977 A1 | 3/2010 | Stahmann |
| 2010/0069980 A1 | 3/2010 | Stahmann |
| 2010/0069984 A1 | 3/2010 | Stahmann |
| 2010/0069985 A1 | 3/2010 | Stahmann |

OTHER PUBLICATIONS

European Search Report dated May 31, 2013, 6 pages.

*Primary Examiner* — Scott Getzow
(74) *Attorney, Agent, or Firm* — ARC IP Law, PC; Joseph J. Mayo

(57) ABSTRACT

At least one embodiment of the invention relates to a cardiac stimulator comprising at least one stimulation unit to deliver subthreshold stimulation pulses for a cardiac contractility modulation therapy via at least two stimulation electrode poles, and at least one sensing unit to detect cardiac electrical or mechanical actions. The at least one sensing unit detects signals characteristic of cardiac action and comprises, or is connected to, an evaluation unit that evaluates signals detected by the sensing unit and supplies a corresponding evaluation result signal. The cardiac stimulator further comprises a therapy control unit to control a respective cardiac contractility modulation therapy depending on a respective evaluation result signal. A respective cardiac contractility modulation therapy is activated/deactivated depending on a stimulation success/failure of a suprathreshold stimulation, and/or therapy parameters of a respective cardiac contractility modulation therapy are selected and/or adjusted depending on the respective evaluation result signal.

13 Claims, 5 Drawing Sheets

CARDIAC STIMULATOR FOR CARDIAC CONTRACTILITY MODULATION

This application claims the benefit of U.S. Provisional Patent Application 61/599,432 filed on 16 Feb. 2012, the specification of which is hereby incorporated herein by reference.

BACKGROUND OF THE INVENTION

1. Field of the Invention

At least one embodiment of the invention relates to a cardiac stimulator comprising at least one stimulation unit, at least three stimulation electrode poles and at least one electrode lead. The at least one stimulation unit is connected or to be connected to the at least three stimulation electrode poles via the at least one electrode lead and is configured to deliver subthreshold stimulation pulses for a cardiac contractility modulation (CCM) therapy via the at least two stimulation electrode poles.

2. Description of the Related Art

Implantable cardiac stimulators in the form of cardiac pacemakers or cardioverters/defibrillators are common in the field of art. Such cardiac stimulators are generally connected to electrode leads, which have stimulation electrodes, and optionally include additional defibrillation electrodes, in a ventricle of a heart or in the direct vicinity thereof. Via a stimulation electrode, a cardiac pacemaker can deliver an electrical stimulation pulse to the muscle tissue of a ventricle, so as to evoke a stimulated contraction of the ventricle, provided that the stimulation pulse is sufficiently intense and the heart muscle tissue (myocardium) is not presently in a refractory phase. Within the scope of this description, such a stimulated contraction of a ventricle is referred to as a stimulated event, and a stimulation pulse that has sufficient intensity to evoke a stimulated contraction of a ventricle is referred to as "suprathreshold". When a natural contraction of the ventricle occurs, it is referred to as an intrinsic activity, or as a natural or intrinsic event, within the scope of this description. A contraction of the right atrium of a heart, for example, is referred to as an atrial event, which can be a natural atrial event, for example, or—in the case of an atrial cardiac pacemaker—a stimulated atrial event. Similarly, a distinction can be made between natural (intrinsic) and stimulated left-ventricular and right-ventricular events.

Starting from the excitation site, a local excitation of the myocardium spreads in the myocardium by way of stimulus conduction and results in a depolarization of the muscle cells, and hence in a contraction of the myocardium. After a short time, a repolarization of the muscle cells occurs, and hence a relaxation of the myocardium. During the depolarization phase, the myocardium cells are not receptive to excitation, as they are refractory. The period is referred to as a refractory period. Electrical potentials accompanying the depolarization and repolarization can be detected and the temporal curves thereof—an electrocardiogram—can be evaluated.

An electrocardiogram shows action potentials that reflect a depolarization of the myocardial cells and accompany a contraction of the ventricle reflectled in a Q-wave, while the repolarization of the myocardial cells accompanying the relaxation of the myocardium is reflected in a T-wave.

In healthy people, the respective cardiac rhythm is determined by a sinoatrial node controlled by the autonomic nervous system. By way of stimulus conduction, the sinoatrial node excites the right atrium of a human heart, and an AV node excites the (right) ventricle of the heart. A natural heart rhythm originating from the sinoatrial node is therefore also referred to as a sinus rhythm and results in respective natural contractions of the respective ventricle, that can be detected as natural (intrinsic) events.

Such natural (intrinsic) events are detected by measuring the electrical potentials of the myocardium of the respective ventricle using sensing electrodes, that are part of a corresponding electrode lead. The sensing electrodes can also be the stimulation electrodes and be used alternately as stimulation and as sensing electrodes. Sensing—for example the perception of intrinsic events—is typically carried out by a sensing electrode pair, which is formed by two adjoining electrodes, more specifically a tip electrode and a ring electrode, of which the tip electrode is also used as the stimulation electrode. In this way, a bipolar measurement of an intracardiac electrocardiogram (IEGM) is obtained. The sensing and the stimulation in the ventricle take place with the aid of a ventricular electrode lead and the stimulation and the sensing in the atrium (in the right atrium) take place with an atrial electrode lead, that are connected separately to the respective cardiac stimulator. Additionally, a left-ventricular electrode lead may be provided, which typically projects over the coronary sinus and a lateral vein branching off the coronary sinus, and into the vicinity of the left ventricle. In the vicinity of the left ventricle, the left-ventricular electrode lead can comprise a small-surface-area stimulation and/or sensing electrode.

With respect to the terms used herein, it shall be pointed out that within the scope of this text the terms stimulation electrode or sensing electrode refer to a respective electrode pole on an electrode lead, wherein stimulation pulses are delivered or electrical potential is taken up. It is also be pointed out that it is also customary to refer to an electrode lead used for stimulation as a "stimulation electrode".

During operation of the cardiac stimulator, the sensing electrodes are connected to corresponding sensing units, which are configured to evaluate a respective electrocardiogram recorded using a sensing electrode (or a sensing electrode pair) and in particular to detect intrinsic atrial or ventricular events; natural atrial or ventricular contractions. This is done, for example, by a threshold comparison, wherein an intrinsic event is detected when a respective intracardiac electrocardiogram exceeds a suitably predefined threshold.

The respective intrinsic atrial heart rate (atrial frequency) or ventricular heart rate (ventricular frequency) can be derived from the frequency at which the atrial or ventricular events follow each other, and tachycardia, for example, can thus be detected.

In typical demand pacemakers, the detection of natural events is also used to suppress (inhibit) the delivery of stimulation pulses to a corresponding ventricle, if the natural event is detected during a time window prior to the planned delivery of a stimulation pulse to the ventricle. In rate-adaptive cardiac pacemakers, the time at which a respective stimulation pulse is delivered is scheduled as a function of a respective stimulation rate, corresponding to the physiological need of a patient. For example, it is greater with greater exertion. For this purpose, a cardiac stimulator can be equipped with one or more activity sensors, which can be a CLS sensor, for example, which will be described in more detail hereafter.

The natural effect of the autonomic nervous system on the heart rate, which is reproduced by a rate-adaptive cardiac stimulator, is referred to a chronotropy.

In addition to the chronotropy, the cardiac performance is also determined by the contractility of the heart, referred to as inotropy.

To determine the contractility of a heart, it is typical to arrange an impedance or conductivity measuring unit in a housing of a cardiac stimulator (for example an implantable cardiac pacemaker). The unit is configured to generate a unipolar or bipolar impedance or conductivity curve signal. For this purpose, several impedance or conductivity values are measured, or a corresponding impedance or conductivity curve is measured, during at least one cardiac cycle. This is done either in a unipolar manner by measuring between a neutral electrode and a measuring electrode, or between two measuring electrodes. Moreover, an evaluation unit is arranged in the housing, to evaluate the impedance or conductivity curve and derive a contractility value from the impedance or conductivity curve. Electrotherapy devices, which are able to determine the contractility of a heart, provide the option to adapt a therapy to be delivered by the electrotherapy device to the respective contractility state of the heart of the patent.

As indicated above, the contractility describes the inotropic state of a heart. The contractility influences the force and speed of a myocardial contraction. Contractility is controlled by three mechanisms:

direct control by the autonomic nervous system (ANS),
the so-called Frank-Starling mechanism and
the so-called Bowditch effect (force-heart rate coupling).

The primary mechanism, controlling the circulatory system regulation through the autonomic nervous system, increases the contractility and the heart rate when an increased metabolic need exists, for example during physical exertion, so as to ensure suitable blood supply. In healthy people, the inotropy of the heart thus causes a rise in the contractility due to increased physiological demand.

In patients with chronic heart failure (HF), the myocardial contractility decreases to a low level and the interventricular synchronization worsens. This is accompanied by a low ejection fraction (EF) as well as by a low quality of life and high mortality. HF is common among the population. Recently, HF patients are treated with resynchronization therapy devices, for example 3-chamber cardiac pacemakers or defibrillators. The objective of such a therapy is to synchronize the two ventricles of a heart by way of biventricular stimulation so as to improve the time response of the ventricles and consequently cardiac performance. Such a therapy is also referred to as cardiac resynchronization therapy (CRT). Cardiac resynchronization therapy (CRT) is sufficiently known and is provided, for example, by BIOTRONIK CRT-D implants (Lumax HF-T).

Cardiac resynchronization therapy (CRT) is a special form of the more general cardiac rhythm management (CCM), which also includes, for example, simple stimulation of only one ventricle to treat bradycardia. A CRM stimulator can therefore also be a single-chamber cardiac pacemaker.

Because the contractility of the heart can be controlled physiologically by the autonomic nervous system, the detection of the contractility can also be utilized to adjust a physiologically adequate stimulation rate in rate-adaptive cardiac pacemakers. This type of stimulation rate control, as addressed above, is also known as closed loop stimulation (CLS).

For CLS, the intracardiac impedance curve after start of the ventricle contraction is measured. This measurement is carried out both for intrinsic and for stimulated events. There is a direct dependency between the right-ventricular impedance curve and the contraction dynamics. The contraction dynamics, in turn, is a parameter for the stimulation of the heart by the sympathetic nervous system.

Closed loop stimulation is, as mentioned above, the control of the stimulation rate with a rate-adaptive cardiac pacemaker.

Cardiac contractility modulation (CCM) therapy mainly used to increase the contractility of a ventricle.

The company Impulse Dynamics, for example, offers an OPTIMIZER system for CCM therapy. This system comprises a stimulation pulse generator, connected to three electrodes, one of which one is arranged during operation in the atrium and on the septum of the right ventricle of a patient. The principle of the therapy is based on a delivery of biphasic stimulation pulses having amplitudes of 7V to 10V and a total pulse duration of ~20 ms in the absolute refractory period of the ventricle with the goal of increasing contractility. The therapy is delivered for certain periods of time of the day (for example, alternately 1 hour on, 1 hour off).

The principle of cardiac contractility modulation therapy is described, amongst others, in U.S. Pat. No. 6,317,631 B1.

The effect of the CCRM therapy is based—according to present assumptions—on a modification of the cellular calcium ion exchange and thus results in an increased contraction force, which could also result in a therapeutic benefit with any existing atrial fibrillation. While this has not yet been clinically proven, it is understood pathophysiologically.

Patent Application Publication Nos. U.S. 2010/0069977 A1, U.S. 2010/0069980 A1, U.S. 2010/0069984 A1 and U.S. 2010/0069985 A1 describe methods for delivering CCM stimulation as needed. They describe, in general terms, the use of physiological sensors, kidney or heart function sensors, electrolyte sensors, serum sensors (for example creatinine), neurosensors (vagus, sympathetic nervous system), adverse event detectors, worsening heart failure sensors, MRI sensors, activity sensors, sleep apnea sensors, ischemia sensors, sensors for metabolic needs, and infarction sensors, as well as heart rhythm-dependent CCM controllers. The aforementioned prior art also describes the disabling of the CCM therapy when atrial fibrillation or atrial arrhythmia is detected (e.g. see U.S. 2010/0069977, FIG. 20A and paragraph [0332]). Similarly, the following description addresses, in very general terms, the possible combination of CCM with other stimulation and electrotherapy forms such as CRT, ICD and neurostimulation. Patent Application Publication Nos. U.S. 2010/0069977 A1, U.S. 2010/0069980 A1, U.S. 2010/0069984 A1 and U.S. 2010/0069985 A1 describe the disabling of the CCM therapy when atrial fibrillation or atrial arrhythmia is detected, however the reason for CCM disabling is not addressed in detail.

Patent Application Publication Nos. U.S. 2010/0069977 A1, U.S. 2010/0069980 A1, U.S. 2010/0069984 A1 and U.S. 2010/0069985 A1 also describe the possible combination of CCM and CRT stimulation in a device.

CCM stimulation pulses are normally delivered in the absolute refractory period of a respective ventricle. These pulses can thus be prevented from inducing arrhythmia.

The CCM system presently available on the market (Optimizer III by Impulse Dynamics) synchronizes the CCM pulses by sensing of septal excitation using a local CCM electrode.

The inventor has recognized the following disadvantages of known CCM stimulators:

With the aforementioned method of CCM synchronization, sensing errors can cause the CCM pulses to be delivered even outside the absolute refractory period. This can have a proarrhythmic effect and induce ventricular tachycardia or ventricular fibrillation.

This risk is increased especially when using CCM stimulation together with additional stimulators, such as a biventricular pacemaker or defibrillator, because delivery of sub-threshold stimuli can be sensed via the CCM system, which could trigger delivery of a CCM pulse.

A further disadvantage of the CCM therapy consists in the necessity to implant two additional stimulation electrodes at the ventricular septum. With the simultaneous use of an ICD or CRT-D, the number of implanted electrodes becomes very large.

Contrary to other CRM stimulators, no stimulation success control is known for the present CCM system. The therapy parameters are established empirically and at best adapted to the clinical long-term progression. Device-internal optimization of the therapy does not exist as of yet.

Based on the disadvantages of the prior art that the inventor has recognized, it is the objective of at least one embodiment of the invention to create an improved cardiac stimulator for cardiac contractility modulation therapy.

BRIEF SUMMARY OF THE INVENTION

According to at least one embodiment of the invention, this objective is achieved by a cardiac stimulator that comprises at least one stimulation unit, connected to at least three stimulation electrode poles via at least one electrode lead. The cardiac stimulator is configured to deliver subthreshold stimulation pulses for a cardiac contractility modulation therapy via at least two stimulation electrode poles, and said at least one sensing unit to detect electrical or mechanical actions of the heart, which are preferably connected to the three stimulation electrode poles. The sensing unit is configured to detect signals characteristic of a heart action and comprises, or is connected to, an evaluation unit configured to evaluate signals detected by the sensing unit and to supply a corresponding evaluation result signal. In addition, the cardiac stimulator comprises a therapy control unit, connected to the stimulation unit and the evaluation unit, and is configured to control a respective cardiac contractility modulation therapy depending on a respective evaluation result signal of the evaluation unit. More specifically, such that a respective cardiac contractility modulation therapy is activated or deactivated depending on a stimulation success or failure of a suprathreshold stimulation, and/or such that therapy parameters of a respective cardiac contractility modulation therapy are selected and/or adjusted depending on the respective evaluation result signal.

Such a cardiac stimulator, in one variant, offers an advantage of significantly lowering the proarrhythmic risk of CCM stimulation with simultaneous antibradycardia or CRT stimulation, by disabling CCM stimulation with a possibly unreliable synchronization due to a lack of stimulation success of a suprathreshold stimulation.

Such a cardiac stimulator, in another variant, additionally offers the advantage of being able to optimize the CCM therapy automatically and while in progress.

In a combination of both variants, such a cardiac pacemaker has the advantage of being able to optimize the CCM therapy automatically and while in progress, and, at the same time, eliminate a potentially proarrhythmic effect of the CCM stimulation in a combination therapy device.

The proposed optimization of the CCM therapy by the therapy control unit, in response to signals detected by the sensing unit, is based on the CCM explanatory model that CCM stimulation during the absolute refractory period causes a homogenization of the excitation state of the myocardial cells (at least locally) and thereby promotes intraventricular and interventricular excitation synchronization. Additionally, it can be assumed that such a homogenization can also be evoked by way of alternative stimulation vectors. Proof of the CCM therapy success required for automatic therapy optimization can be supplied by measuring intraventricular and/or interventricular depolarization times and/or repolarization times. With therapy success it can be assumed that these times, measured over various vectors, conform to each other.

For such a therapy optimization, notably an implantable CCM therapy device comprising at least two or more CCM stimulation current paths is provided, such as at least three or more CCM stimulation electrode poles. At least three of the CCM stimulation electrode poles and/or further sensing electrode poles are connected to a sensing unit, wherein the sensing unit is configured to determine the times of a characteristic intrinsic or stimulated cardiac excitation at these points and to carry out a propagation time measurement or determine alternative signal characteristics.

A therapy control unit that is connected to the sensing unit is configured to vary the CCM stimulation vectors and/or parameters as a function of the propagation time measurement/signal characteristics.

The CCM stimulation vectors are preferably derived from the electrode pole combinations present in a CRT system.

Preferred embodiment variants of the invention include the following:

The sensing unit is preferably designed to detect signals characteristic of cardiac action at the respective site, or in the direct vicinity of the at least three stimulation electrode poles. The sensing unit is preferably configured to detect times of a characteristic intrinsic or stimulated cardiac excitation at the at least three stimulation electrode poles. For this purpose, the sensing unit is connected to the at least three stimulation electrode poles and/or sensing electrode poles adjoining the same and is configured to detect electrical potentials (action potentials) characteristic of cardiac action via the at least three stimulation electrode poles.

As indicated above, the sensing unit preferably comprises an evaluation unit, or is connected to an evaluation unit, wherein the evaluation unit is configured to determine a propagation time (time lag) between at least two signals detected by the sensing unit and to supply a corresponding evaluation result signal.

As an alternative or in addition, it is also possible for the sensing unit to comprise an evaluation unit, or be connected to an evaluation unit, that is configured to determine signal characteristics of at least two signals detected by the sensing unit and to supply a corresponding evaluation result signal.

The therapy control unit may be configured, in all instances, to select two of the stimulation electrode poles for a cardiac contractility modulation therapy which results in the balanced intraventricular and/or interventricular depolarization times and/or repolarization times.

In a particular case, the sensing unit is configured to determine the duration of a repolarization (for example the duration of the T wave) in at least two sites. The therapy control unit is then preferably configured to select and/or adjust therapy parameters of a cardiac contractility modulation therapy so that a minimum of repolarization times is obtained.

As an alternative or in addition, the therapy control unit can also be configured to select and/or adjust therapy parameters of a cardiac contractility modulation therapy so that a homogenization of repolarization times is obtained.

The therapy control unit can also be configured to select and/or adjust therapy parameters of a cardiac contractility modulation therapy so that a maximum of a slew rate of an action potential detected by the sensing unit is obtained.

According to a further alternative or an additional option, the therapy control unit is configured to select and/or adjust therapy parameters of a cardiac contractility modulation therapy so that a homogenization of the slew rates of action potentials detected by the sensing unit is obtained.

It may also be advantageous for the therapy control unit to select and/or adjust therapy parameters of a cardiac contractility modulation therapy so that a maximum of the action potential duration of an action potential detected by the sensing unit is obtained.

Correspondingly, it is preferred if the sensing unit, or the evaluation unit thereof, to determine the duration of repolarization (for example the duration of the T wave) in at least two points. The therapy optimum can be defined by a minimum of the repolarization times and/or by a homogenization of the repolarization times and/or by a maximum of the slew rate of the action potential land/or by a homogenization of the slew rate of the action potential and/or by a maximum of the action potential duration and/or by a homogenization of the action potential duration.

According to a particularly preferred embodiment variant, the cardiac stimulator comprises at least one stimulation unit for delivering suprathreshold stimulation pulses and the evaluation unit is configured to evaluate signals that were detected by the sensing unit after delivery of a suprathreshold stimulation pulse with respect to a success of the stimulation, and to supply a corresponding evaluation result signal. The therapy control unit is configured to deactivate a respective cardiac contractility modulation therapy at least for a respective cardiac cycle if the evaluation result signal does not show any stimulation success and/or to allow a respective cardiac contractility modulation therapy for at least one respective cardiac cycle, only if the evaluation result signal shows effective stimulation in at least one ventricular stimulation site, or all those sites which are used.

As mentioned above, such a cardiac stimulator offers the advantage of significantly lowering the proarrhythmic risk of CCM stimulation with simultaneous antibradycardia or CRT stimulation by disabling CCM stimulation with a possibly unreliable synchronization due to a lack of stimulation success of a suprathreshold stimulation.

The cardiac stimulator is thus preferably an implantable combination therapy device for CCM therapy and for simultaneous antibradycardia and/or CRT stimulation, comprising a CCM stimulation and synchronization unit and a CRT/bradycardia stimulation unit. Furthermore, the stimulator additionally comprises a stimulation success control unit, at least for ventricular stimulation, which is configured as a sensing unit and the correspondingly designed evaluation unit. The therapy control unit is then configured to allow CCM stimulation in the current cardiac cycle only if the stimulation success control unit previously indicated an effective stimulation of all ventricular stimulation sites that are used. Otherwise CCM stimulation is discontinued.

Stimulation success control is preferably carried out by the sensing unit and the evaluation unit by evaluating evoked potentials at the respective electrode. As an alternative or in addition, the stimulation success control can be carried out by evaluating a CLS signal. A further alternative is a stimulation success control by evaluating an HDS signal, by verifying an actual contraction.

Moreover, the cardiac stimulator preferably has a memory and is configured to store an inhibition of the CCM stimulation in a statistic, together with the reason for the inhibition.

Overall, this provides a cardiac stimulator for an improved CCM therapy. Using automatically switchable CCM current paths, CCM effectivity control and a CCM safety stimulation device automatically optimizes the CCM therapy.

BRIEF DESCRIPTION OF THE DRAWINGS

The invention will now be described in more detail hereafter by way of example based on exemplary embodiment with reference to the figures, wherein.

DETAILED DESCRIPTION OF THE INVENTION

Figure 1:
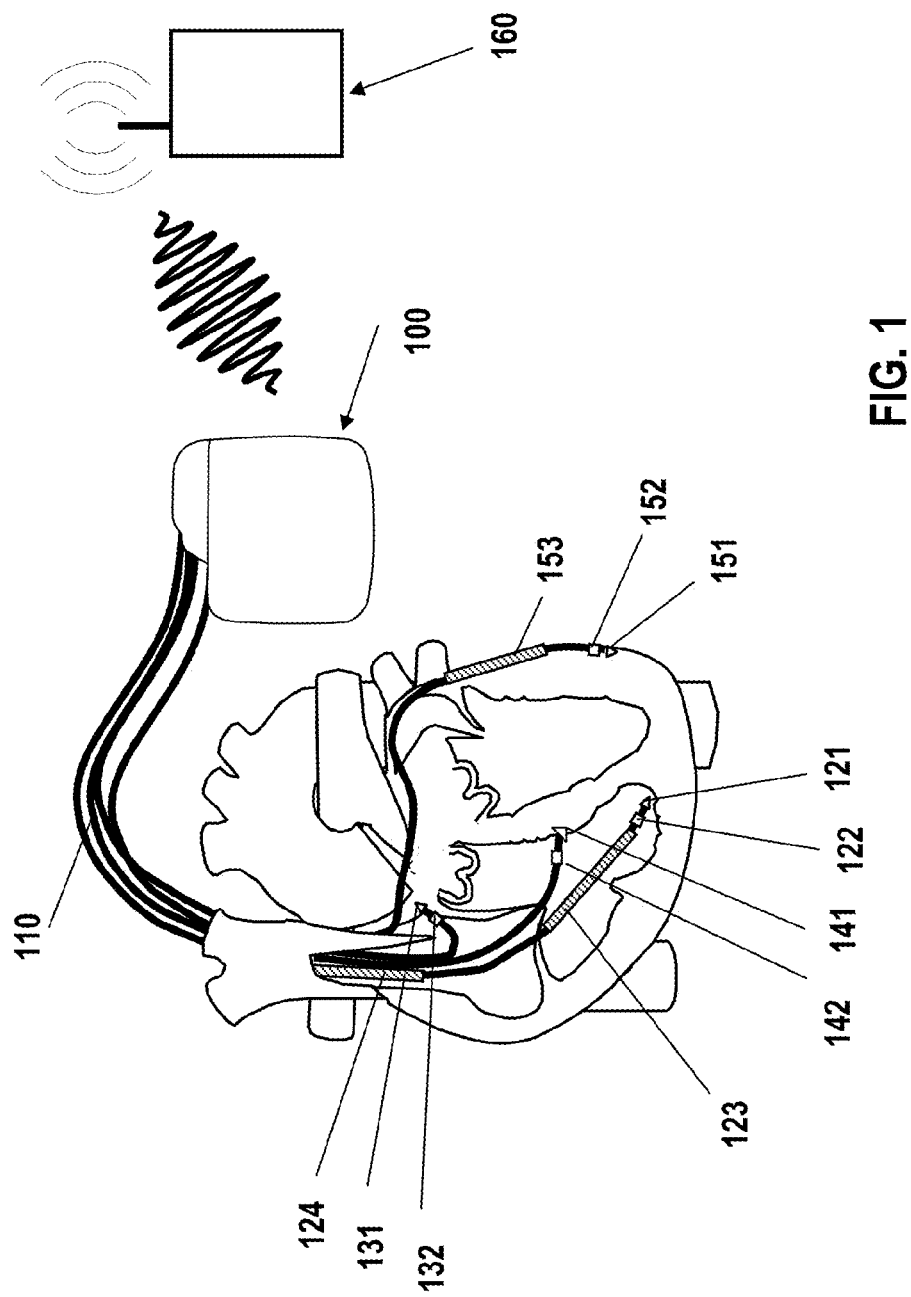
FIG. 1: shows a CRT-CCM stimulator.

FIG. 1 shows a cardiac stimulator of a triple-chamber ICD system with integrated CRT-CCM function as an implementation example. A generator 100 is connected to several implantable electrode leads 110. For the purpose of right-ventricular sensing and stimulation, a right-ventricular electrode lead comprises a right-ventricular tip electrode 121 and a right-ventricular ring electrode 122 at the distal end of the right-ventricular electrode lead. In the case of a cardiac resynchronization therapy (CRT), right-ventricular stimulation pulses for the biventricular CRT stimulation are delivered via the right-ventricular tip electrode 121. A distal shock coil 123, and optionally a proximal shock coil 124, is arranged on the right-ventricular electrode lead for delivering defibrillation shocks. The generator housing 100 forms the counter-electrode for the delivery of defibrillation shocks.

At the distal end, a right-atrial electrode lead has a bipolar sensing and stimulation pole comprising a right-atrial tip electrode 131 and a right-atrial ring electrode 132 and is used to sense atrial rhythm and, as needed, atrial stimulation.

The system further comprises a left-ventricular or CS (coronary sinus) electrode for delivering left-ventricular stimulation pulses for CRT via a left-ventricular tip electrode 151 and a left-ventricular ring electrode 152. A left-ventricular shock coil 153 is optionally provided for more effective defibrillation cardioversion.

For CCM stimulation, one or more right-ventricular septal electrode leads are provided, which deliver respective CCM pulses to the ventricular septum via a septal tip electrode 141 and a septal ring electrode 142. However, it also possible to use more than two septal CCM stimulation poles, or the additional electrode poles (121, 122, 123, 151, 152, 153) used for CRT-D stimulation can be used for CCM vector switching.

A sensing and evaluation unit (250, 260, 270, 280; 580) is connected to at least two, and more preferably all, stimulation electrode poles (121, 122, 141, 142, 151, 152) so as to detect the local depolarization speeds and repolarization parameters.

A wireless bidirectional telemetry unit is provided for communicating with external programming devices and control and data transmission devices 160.

Figure 2:
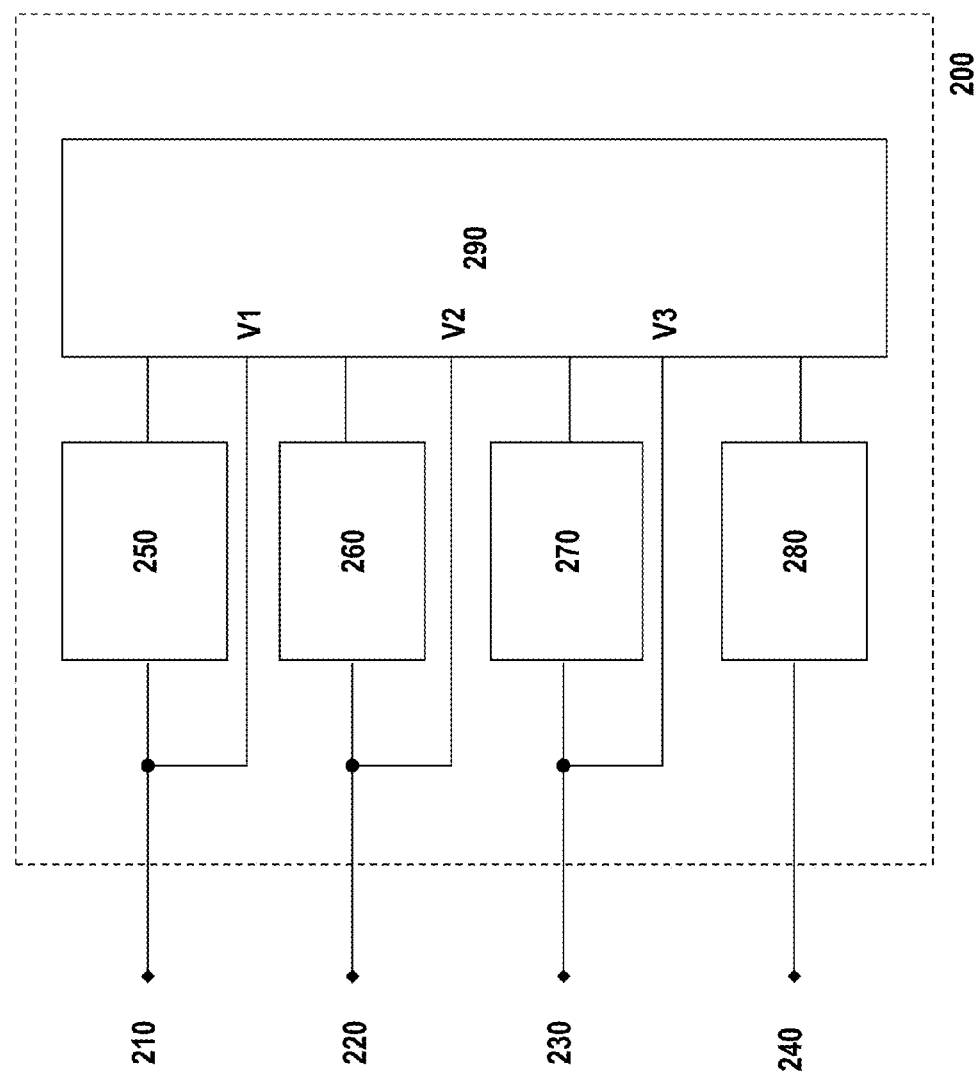
FIG. 2: shows a block diagram of an automatic therapy optimization.

FIG. 2 is a block diagram comprising the components of the cardiac stimulator that are used to automatically optimize a CCM therapy. Here, a CCM generator 200 is connected to a total of four electrode poles (210, 220, 230, 240). Three electrode poles (210, 220, 230) can be selectively used for delivering the CCM stimulation pulses, whereby switchable stimulation vectors are obtained. All four electrode poles are connected to a respective identical sensing unit (250, 260, 270, 280). These sensing units do not include an evaluation unit, which is not explicitly shown, and preferably detect a repolarization parameter from the intracardiac electrogram at the respective electrode pole and forward this information to a CCM therapy control unit 290 in the form of a respective evaluation result signal. The CCM therapy control unit 290 evaluates the information about the repolarization and, via a common search technique, optimizes the pulse parameterization that is optimal for the CCM therapy, and more particularly, it determines the stimulation vector (V1, V2, V3) that is most effective and also most efficient in terms of energy consumption.

Figure 3:
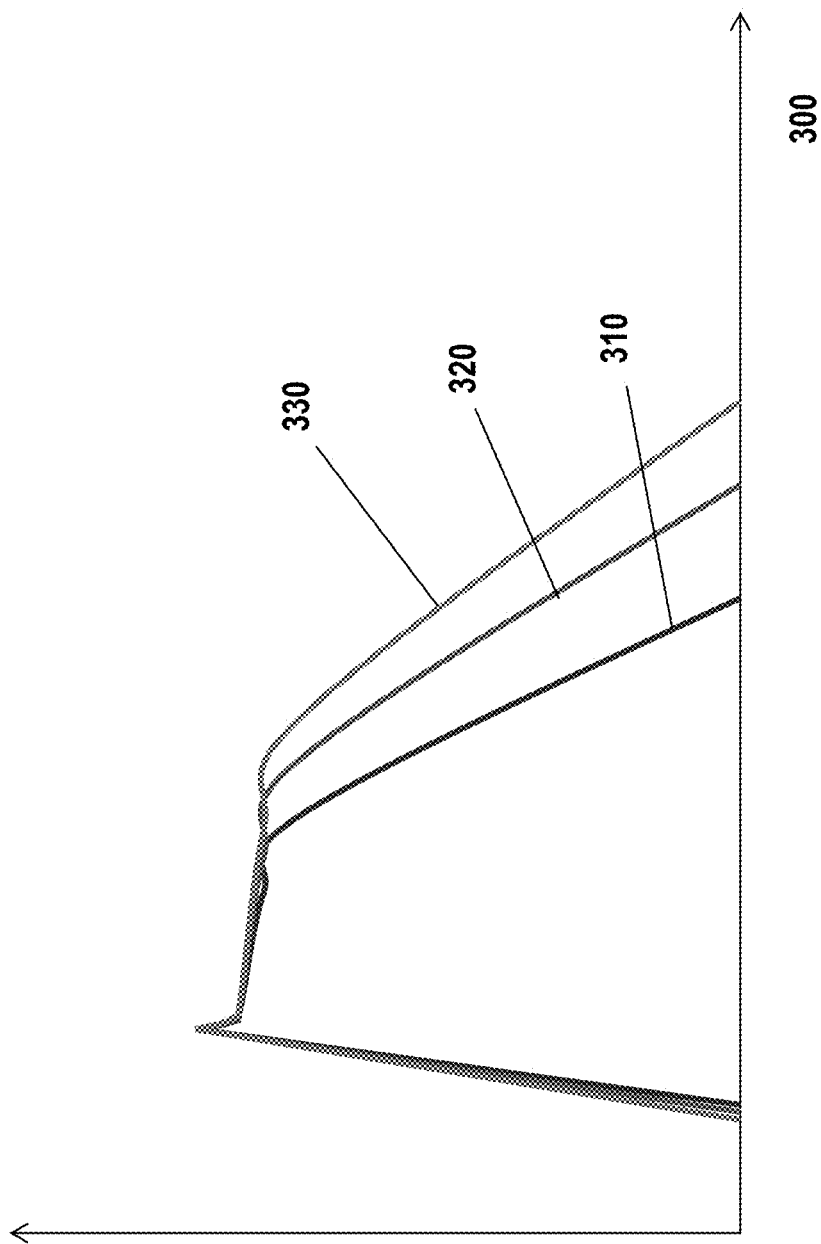
FIG. 3: is an example of an action potential with ineffective CCM stimulation.
Figure 4:
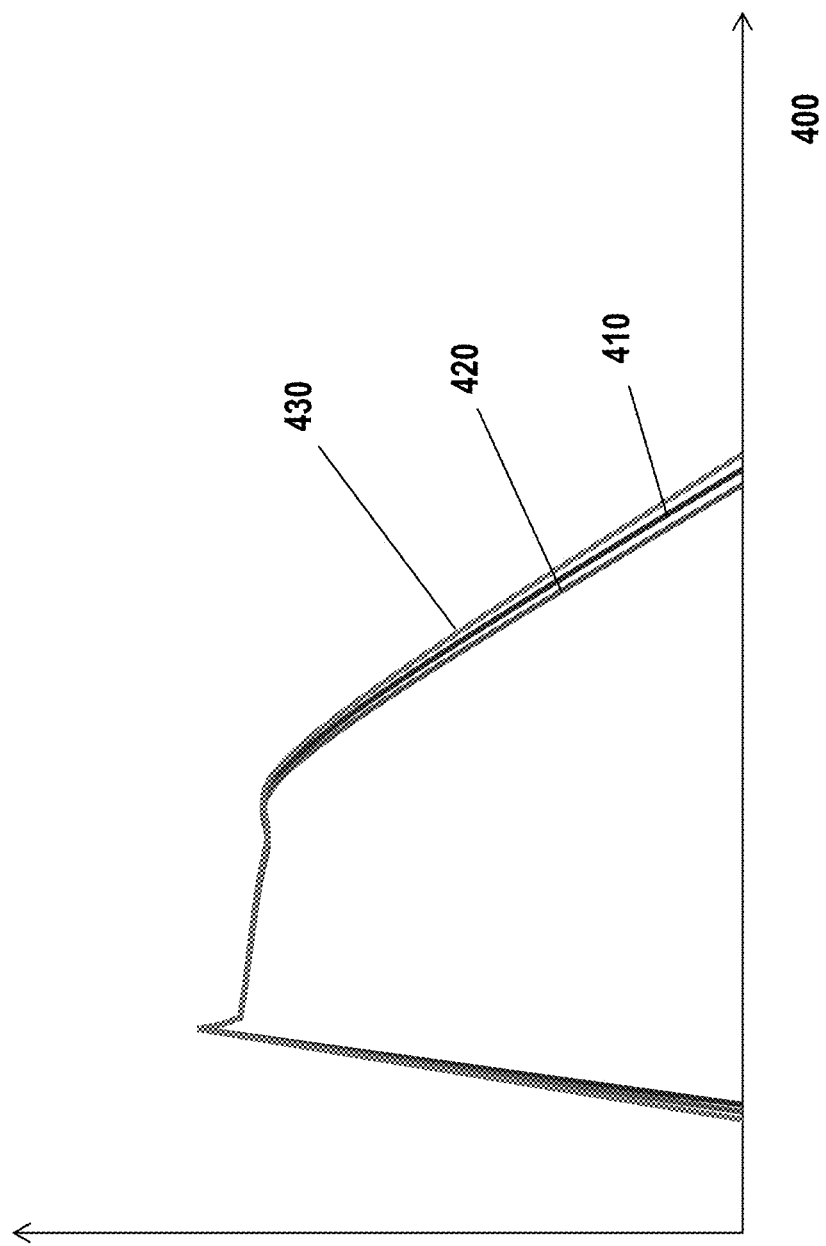
FIG. 4: is an example of an action potential with effective CCM stimulation.

FIG. 3 and FIG. 4 show an assumed control variable for the implementation example based on the example of action potential curves.

In the example shown in FIG. 3, the repolarization is relatively broad (310, 320, 330), so that a less effective CCM therapy can be assumed here.

This is different in the example shown in FIG. 4: The repolarizations are considerably more homogeneous (410, 420, 430) by comparison, whereby a positive effect of the CCM therapy is demonstrated.

As an alternative, the CCM therapy control unit can also compare the signal propagation times of various excitation sections at the individual electrode poles, or between different vectors, as the control variable. The objective of optimizing the therapy is to homogenize the signal propagation times.

Figure 5:
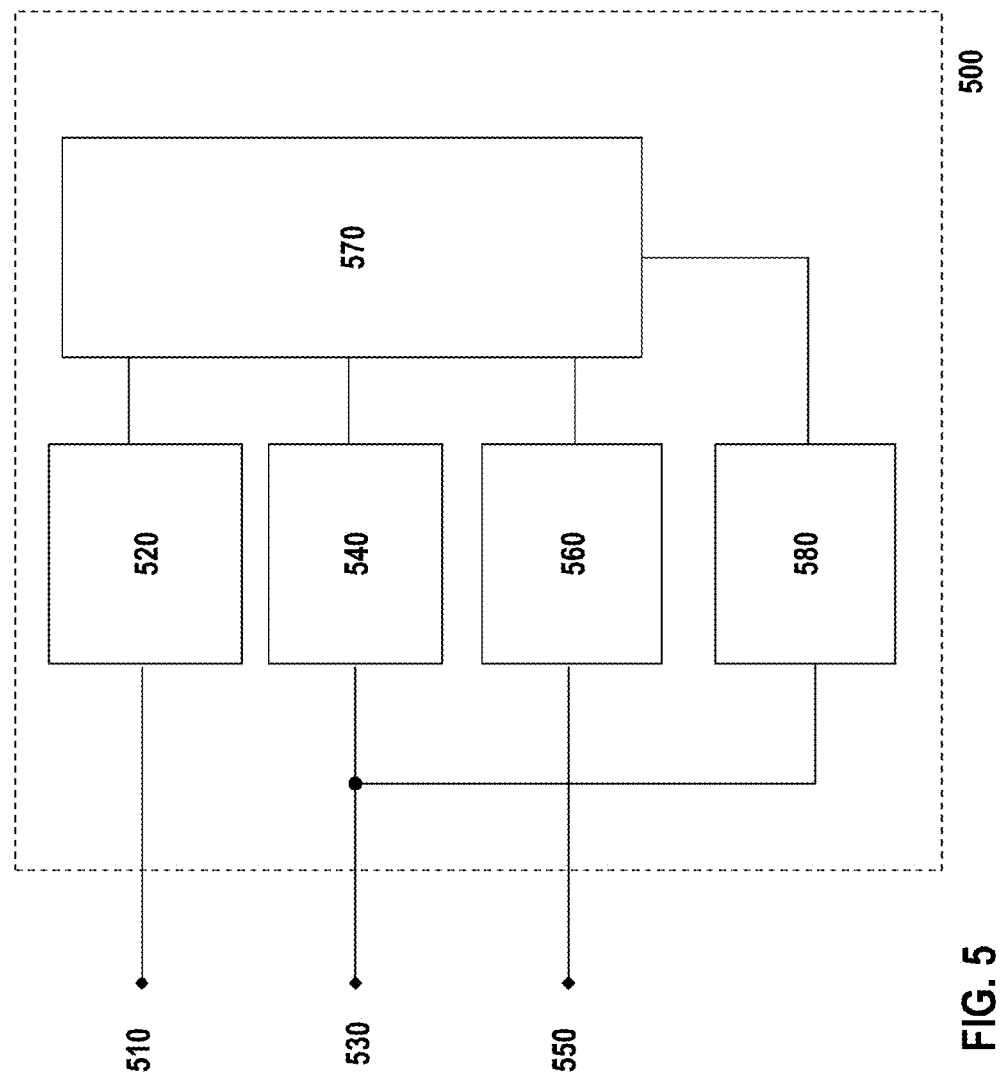
FIG. 5: is a block diagram of a CCM inhibition with a lack of stimulation success of CRM stimulation.

FIG. 5 shows, in a separate block diagram, the components of a combined CRT-CCM stimulator that are used for CCM therapy inhibition in the case of unsuccessful CRT stimulation. The CRT-CCM stimulator shown in FIG. 5 comprises at least the following components: a generator 500; a right-atrial electrode lead 510, connected to an atrial sensing and stimulation unit for classifying the atrial rhythm and for atrial stimulation as needed; right-ventricular and left-ventricular electrode terminals 530, connected to a biventricular sensing and stimulation unit for sensing and classifying the ventricular rhythm and the biventricular CRT stimulation; and one or more CCM electrodes, connected to a CCM stimulation unit 560; wherein the atrial sensing and stimulation unit 520, the biventricular sensing and stimulation unit 540, and the CCM stimulation unit 560 are connected to a therapy control unit 570 for controlling and synchronizing the CRT and CCM therapies.

The combined CRT-CCM stimulator additionally comprises a stimulation success control unit 580, which is also connected to the ventricular electrode terminals 530. The stimulation success control unit evaluates the stimulation success of the ventricular stimulation for each cycle and for each ventricular electrode and forwards this evaluation to the therapy control unit 570.

The therapy control unit inhibits the CCM stimulation when no stimulation success in the current cardiac cycle on at least one of the ventricular electrodes exists.

The block diagram of FIG. 5 can be combined with the block diagram of FIG. 2.

A cardiac stimulator described herein has the advantage of CCM therapy automatically optimized by the implant and, optionally, the number of electrode leads that are required can be reduced in a combination therapy device.

Such a cardiac stimulator moreover offers the advantage that CCM stimulation can be employed in a combination therapy device together with CRT stimulation or antibradycardia stimulation, without any pro-arrhythmic risk.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A cardiac stimulator, comprising
at least three stimulation electrode poles;
at least one electrode lead;
at least one stimulation unit connected to said at least three stimulation electrode poles via said at least one electrode lead;
wherein the at least one stimulation unit is configured to deliver subthreshold stimulation pulses for a cardiac contractility modulation therapy via at least two of the at least three stimulation electrode poles;
at least one sensing unit configured to detect electrical or mechanical actions of the heart and configured to detect signals characteristic of a heart action;
wherein the at least one sensing unit comprises, or is connected to, an evaluation unit configured to evaluate signals detected by the sensing unit, to evaluate a stimulation success or failure of a suprathreshold stimulation for each of said at least three stimulation electrode poles, and to supply a corresponding evaluation result signal; and
a therapy control unit connected to the stimulation unit and the evaluation unit, wherein the evaluation unit forwards said evaluation result signal to said therapy control unit;
wherein the therapy control unit is configured to control a respective cardiac contractility modulation therapy dependent on the corresponding evaluation result signal of the evaluation unit,
wherein the respective cardiac contractility modulation therapy is configured to be activated or deactivated dependent on said stimulation success or failure of said suprathreshold stimulation,
wherein therapy parameters of the respective cardiac contractility modulation therapy are selected and/or adjusted dependent on the respective evaluation result signal;
wherein the respective cardiac contractility modulation therapy is optimized automatically and while in progress,
wherein said therapy control unit optimizes the therapy parameters that are optimal for said respective cardiac contractility modulation therapy,
wherein the evaluation unit evaluates signals detected by the at least one sensing unit after delivery of said suprathreshold stimulation pulse with respect to a success of the stimulation, and supplies a corresponding evaluation result signal; and,
wherein the therapy control unit
deactivates a respective cardiac contractility modulation therapy at least for one respective cardiac cycle if the evaluation result signal does not show any stimulation success; and,
allows a respective cardiac contractility modulation therapy for at least one respective cardiac cycle only if the evaluation result signal shows an effective stimulation in at least one ventricular stimulation site, or all sites being stimulated
wherein the a least one sensing unit is further configured to determine the duration of a repolarization in at least two sites, and,
wherein therapy control unit selects and/or adjusts therapy parameters of the cardiac contractility modulation therapy, such that said therapy parameters that are optimal for said respective cardiac contractility modulation therapy are defined by one or more of
- a minimum of repolarization times, in response to said selection and/or adjustment,
- a homogenization of the repolarization times, in response to said selection and/or adjustment,
- a maximum of a slew rate of an action potential detected by the at least one sensing unit, in response to said selection and/or adjustment,
- a homogenization of the slew rates of action potentials detected by the at least one sensing unit, in response to said selection and/or adjustment,
- a maximum of an action potential duration of an action potential detected by the at least one sensing unit in response to said selection and/or adjustment, and,
- a homogenization of the action potential duration of action potentials detected by the at least one sensing unit, in response to said selection and/or a adjustment.

2. The cardiac stimulator according to claim 1, wherein the at least one sensing unit is further configured to detect signals characteristic of cardiac action at a respective site, or in a direct vicinity of the at least three stimulation electrode poles.

3. The cardiac stimulator according to claim 2, wherein the at least one sensing unit is further configured to detect times of a characteristic intrinsic or stimulated cardiac excitation at the at least three stimulation electrode poles.

4. The cardiac stimulator according to claim 3, further comprising sensing electrode poles, wherein the at least one sensing unit is connected to the sensing electrode poles and is further configured to detect electrical potentials characteristic of cardiac action via the at least three stimulation electrode poles and/or the sensing electrode poles.

5. The cardiac stimulator according to claim 1, wherein the evaluation unit is further configured to determine a time lag between at least two signals detected by the at least one sensing unit and to supply a corresponding evaluation result signal.

6. The cardiac stimulator according to claim 1, wherein the evaluation unit is further configured to determine signal characteristics of at least two signals detected by the at least one sensing unit and to supply a corresponding evaluation result signal.

7. The cardiac stimulator according to claim 5, wherein the therapy control unit is further configured to select two of the at least three stimulation electrode poles for a cardiac contractility modulation therapy that results in balanced intraventricular and/or interventricular depolarization times and/or repolarization times.

8. The cardiac stimulator according to claim 1, wherein the therapy control unit is further configured to obtain said minimum of repolarization times, in response to said selection and/or adjustment, such that the respective cardiac contractility modulation therapy is optimized with said optimum defined by said minimum of repolarization times.

9. The cardiac stimulator according to claim 1, wherein the therapy control unit is further configured to obtain said homogenization of the repolarization times, in response to said selection and/or adjustment, such that the respective cardiac contractility modulation therapy is optimized with said optimum defined by said homogenization of the repolarization times.

10. The cardiac stimulator according to claim 1, wherein the therapy control unit is further configured to obtain said maximum of a slew rate of an action potential detected by the at least one sensing unit, in response to said selection and/or adjustment, such that the respective cardiac contractility modulation therapy is optimized with said optimum defined by said slew rate of said action potential.

11. The cardiac stimulator according to claim 1, wherein the therapy control unit is further configured to obtain said homogenization of the slew rates of action potentials detected by the at least one sensing unit, in response to said selection and/or adjustment, such that the respective cardiac contractility modulation therapy is optimized with said optimum defined by said homogenization of the slew rates of said action potentials.

12. The cardiac stimulator according to claim 1, wherein the therapy control unit is further configured to obtain said maximum of an action potential duration of an action potential detected by the at least one sensing unit, in response to said selection and/or adjustment, such that the respective cardiac contractility modulation therapy is optimized with said optimum defined by said maximum of an action potential duration of said action potential.

13. The cardiac stimulator according to claim 1, wherein the therapy control unit is further configured to obtain said homogenization of the action potential duration of action potentials detected by the at least one sensing unit, in response to said selection and/or adjustment, such that the respective cardiac contractility modulation therapy is optimized with said, optimum defined by said homogenization of the action potential duration of said action potentials.

* * * * *